United States Patent [19]
Kilpela et al.

[11] Patent Number: 6,123,708
[45] Date of Patent: Sep. 26, 2000

[54] INTRAMEDULLARY BONE FIXATION ROD

[75] Inventors: Thomas N. Kilpela, Marquette, Mich.; Clayton R. Perry, St. Louis, Mo.; Kenneth A. Davenport; Matthew N. Songer, both of Marquette, Mich.

[73] Assignee: Pioneer Laboratories, Inc., Marquette, Mich.

[21] Appl. No.: 09/243,988

[22] Filed: Feb. 3, 1999

[51] Int. Cl.[7] .................................................. A61B 17/56
[52] U.S. Cl. ................................ 606/62; 606/64; 606/67
[58] Field of Search ................................ 606/62–64, 67, 606/72, 73, 96, 98

[56] References Cited

U.S. PATENT DOCUMENTS

| | | |
|---|---|---|
| D. 379,855 | 6/1997 | Perry . |
| 5,034,013 | 7/1991 | Kyle et al. . |
| 5,041,115 | 8/1991 | Frigg et al. . |
| 5,263,955 | 11/1993 | Baumgart et al. . |
| 5,429,640 | 7/1995 | Shuler et al. . |
| 5,472,444 | 12/1995 | Huebner et al. . |
| 5,505,734 | 4/1996 | Caniggia et al. . |
| 5,697,930 | 12/1997 | Itoman et al. . |
| 5,766,174 | 6/1998 | Perry . |
| 5,971,986 | 10/1999 | Santori et al. ........................ 606/62 |

OTHER PUBLICATIONS

A portion of a catalog of the ORTHoNAIL™ Humeral Nail of Orthologic Company, dated 1996.
A data sheet to the Speedlok Self–Guided Femoral Nail System (2 pages) 1998, General Orthpedics, Inc.
A data sheet entitled The Cane by Acumed (2 pages), Aug. 1996.
A brochure entitled POLARUS by Acumed, Inc. Aug., 1996 (4 pages).
A brochure entitled POLARUS PLUS Surgical Technique of Acumed, Inc. Dec., 1995, (14 pages).
A brochure entitled CHIODO ENDOVIS NAIL CITIEFFE (8 pages, Dec. 1995.
An article of Jeanette E. Dalton et al. entitled "A Biomechanical Comparison of Intramedullary Nailing System For the Humerus".
Journal of Orthopaedic Trauma, vol. 7, No. 4, pp. 367–374 (Nov. 1993).

*Primary Examiner*—Michael Buiz
*Assistant Examiner*—Julian W. Woo
*Attorney, Agent, or Firm*—Gerstman, Ellis & McMillan, Ltd.

[57] ABSTRACT

A nail (or rod) for axial insertion into a large bone for support thereof, which comprises an elongated nail body having a central bore extending through the nail body from the proximal end along a proximal portion of the nail, and typically terminating at point spaced between the ends. The nail may also define a transversely flattened distal portion extending proximally from the distal end. In the embodiment shown, an open slot may extend centrally and longitudinally from the distal end along the distal portion to an inner slot end which is spaced between the ends of the nail. The nail body defines a plurality of transverse holes extending therethrough for receiving bone screws for supporting securance of the nail to a bone while the nail occupies the intramedullar space of the bone.

21 Claims, 1 Drawing Sheet

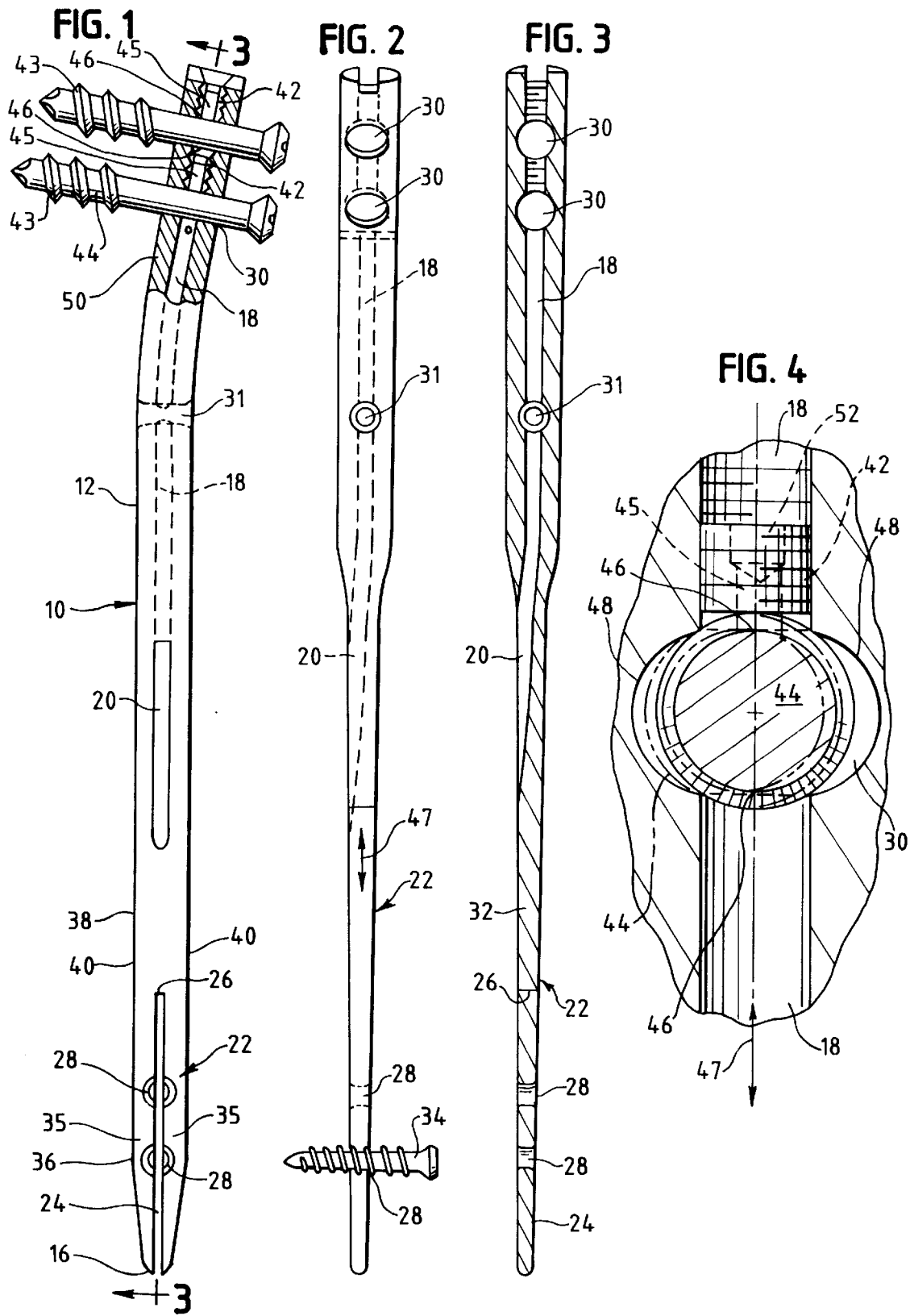

INTRAMEDULLARY BONE FIXATION ROD

BACKGROUND OF THE INVENTION

Intramedullary nails (known also as intramedullary rods) are well known for use in orthopedic surgery for repairing fractures of large bones, particularly the humerus. Recent examples of such intramedullary nails are disclosed in Perry U.S. Des. Pat. No. 379,855, Perry U.S. Pat. No. 5,766,174, and Itouran et al. U.S. Pat. No. 5,697,930, among others. Other humeral nails or rods (for the humerus) are commercially available for clinical use, such as the Ultramodular Trauma System of Howmedica, the modular nail of Richards Company, the Uniflex Humeral Nail of Biomet, and the Polarus Humeral Nail of Acumed.

Humeral nails or rods are used to repair the breakage of a large or long bone such as the humerus by advancing the nail axially through the hollow interior of the bone so that the nail cross the fracture site. Then, screws are applied to the nail through transverse apertures in the nail, extending through the bone on both sides of the site so that the nail is attached to portions of the bone on each side of the fracture, thus securing the bone into a single, immoveable piece once again and allowing healing to take place along the fracture site.

The various designs of intramedullary nail, and specifically humeral nails, which are available and known have certain disadvantages. For example, there is the danger that a humeral nail can have an oversized tip, so that when it is forcefully, longitudinally advanced into the bone interior, the oversized tip can be too large for the size of the bone medulla and split the bone, which can happen without warning. This of course, is a clinical disaster, greatly increasing the severity of the bone injury. With many prior art humeral nails, the problem is difficult to avoid, since the transverse dimensions of the medulla or marrow portion of the bone vary widely from patient to patient.

Also, problems can arise because the transverse bone screws which pass through the humeral nail can be insufficiently solidly retained to the humeral nail, causing the possibility of a small amount of "play" in the system, which of course transfers to the bone. However, if set screws are used in the bore of a tubular humeral nail for transverse screw retention, then it is not possible to use a guidewire system, as is highly desirable in many circumstances to aid in the emplacement of the humeral nail, because when the guidewire passes through the bore of such a humeral nail, the set screw of course interferes with the passage of the guidewire. Thus, although the use of set screws might be desirable to help to stabilize the bond between the emplaced humeral nail and transverse bone screws, this cannot be easily used with a guidewire system.

By this invention, an intramedullary nail (or rod) is provided, and specifically a humeral nail, which can be firmly secured to the transverse bone screws used with such a nail on a reliable basis. Also, the tip of the intramedullary nail of this invention is capable of entering into firm engagement with hard portions of the bone from a location within the medulla of the bone where the marrow resides, without providing so much pressure on the bone that there is a significant risk of fracture due to the outward pressure exerted by the emplaced nail.

DESCRIPTION OF THE INVENTION

By this invention, a rod (Also called a nail) for axial insertion into a large (long) bone is provided for the support thereof. The rod comprises an elongated rod body having a proximal end and a distal end. A central bore extends through the rod body from the proximal end along a proximal portion of the rod, with the bore terminating at a point which is spaced between the ends. The rod also defines a transverse, flattened distal portion which extends from the distal end toward a central portion of the rod. An open slot also extends centrally and longitudinally from the distal end along the distal portion to an inner slot end, which is also spaced between the ends. As is common, the rod body defines a plurality of transverse holes extending therethrough.

Accordingly, the distal portion of the rod, with its open slot, becomes more flexible then the typical distal ends of humeral rods of the prior art. When longitudinally inserted into the bone interior, the distal end can be more easily flexed inwardly by the walls of the hard bone portion outside of the rod, so that the tip of the humeral rod enters into firm, retentative relation with the hard, outer portions of the bone without exerting so much external pressure that there is a risk of bone fracture. Rather, the distal end portion of the rod or nail of this invention, with its slot, exerts a more limited outward pressure against the hard bone exterior, even if the distal end of the rod or nail of this invention turns out to be slightly oversized for the particular bone. Also, the legs of the rod that are defined on either side of the slot can be distracted outwardly as desired by the surgeon, by driving a tapered bone screw between the legs in the slot.

The central bore referred to above in the rod of this invention preferably terminates at an aperture in the side wall of the rod. Thus a rod of this invention can be emplaced using a guidewire technique, where the guidewire has been pre-emplaced in the patient, by advancing the bone along the guidewire, where the guidewire extends through a proximal portion of the rod in a bore thereof, and the guidewire extends along a distal portion of the rod outside of the rod or in the slot described above.

The central bore and the open slot of the rod of this invention may be separated by a partition, so that they are not in open communication with each other. The partition is typically made of the metallic material of the rod. Alternatively, if desired, the open slot may communicate directly with the central bore. In this circumstance, the central bore does not require a side wall aperture since the guidewire can extend through the distal portion of the nail of this invention in the open slot thereof.

At least one of the transverse holes may be located adjacent to the distal end. Such a transverse hole may carry a tapered cortical screw or the like for locking securance of the rod in the bone. Typically, such a transverse hole passes through the open, longitudinally extending slot. In this circumstance, as previously stated the cortical screw can be used to distract the legs or fins of the rod body, which fins are the portions of the rod along each side of the slot. Thus, securance of the rod within the bone can be promoted by the action of such cortical screws positioned transversely in apertures which extend through the slot-defining fins of the rod adjacent to the distal end.

The Side edges of the rod distal portion may be straight. Alternatively, a first portion of the transversely flattened rod distal portion may have a width that is greater than the width of a second portion of the transversely flattened distal portion. The first portion is nearer to the distal end than the second portion, so that the structure of the distal portion of the rod may resemble a paddle with a flaring outer end to an extent. Preferably in this circumstance, the distal portion has opposed, smooth, arcuate side edges defining this paddle shape.

The purpose of such a latter shape, when present, is that the transversely enlarged "paddle" portion of the rod can aid locking in the distal humeral canal in the preferred situation where the rod or nail is for the humerus. The narrower "neck" portion can aid in preventing fracture of the humeral shaft during insertion and afterward, since it may reside in a portion of the medulla of the humerus which is narrower than other portions, so that the narrowed neck portion resides therein without exerting much outward pressure on the bone. Also, the narrowed neck portion provides added resilience to that portion of the rod which is distal to the narrowed neck portion, including the first, wider portion discussed above.

It is also preferred for at least one of the transverse holes to intersect the central bore in the proximal rod portion. A set screw may occupy the bore in a position to retain a bone screw extending through the above transverse hole that intersects the central bore. This may be provided as a factory preinserted or preloaded set screw, to facilitate the surgical procedure.

Also, preferably, such a set screw may carry an axial aperture, to permit a guidewire to extend completely through the central bore despite the presence of the set screw. Thus, the humeral rod may be installed by a guidewire technique, as is frequently a surgical desire, while at the same time the set screw may be pre-emplaced and ready to secure a transverse screw for retaining the rod in the desired position in the humerus or other long bone.

It is also preferred for at least one of the transverse holes which intersect the central bore of the nail to define on each side of the central bore axially spaced first wall sections, which are separated by and connected with circumferentially spaced second wall sections. These sections are proportioned to permit threaded engagement of a screw in the transverse hole by the first wall sections, while the screw is disengaged and spaced from the second sections. Typically, the first wall sections may be almost flat or slightly concave, and the second sections may be more concave, so that the transverse hole forms a substantial oval to avoid second section engagement with a transverse screw extending straight through the hole. This arrangement can be used to allow the transverse screw to rotate about 5 to 30 degrees in each horizontal direction, preferably about 15 degrees, specifically in a horizontal plane which is essentially perpendicular to the longitudinal axis of the rod. At the same time, the screw cannot rotate or otherwise move in a direction transverse to that horizontal plane, but it can rotate about its own axis. Thus, a nail which can carry transverse screws with this characteristic can better accommodate various bone geometries pertaining, for example, to the head of the humerus, when compared with a retention screw in a transverse hole that lacks this characteristic.

The set screw carried in the bore can then be used to reliably hold such a transverse screw in a desired rigid position, once the properly adjusted position of the transverse bone retention screw has been achieved.

DESCRIPTION OF THE DRAWINGS

Referring to the drawings, FIG. 1 is an elevational view, taken partially in longitudinal section, of a bone fixation nail or rod in accordance with this invention;

FIG. 2 is an elevational view of the nail or rod of FIG. 1 rotated 90 degrees about its axis;

FIG. 3 is a longitudinal sectional view of the nail or rod from the view of FIG. 2; and FIG. 4 is an enlarged, detailed, sectional view of a proximal hole for transverse bone screws found in the nail or rod of FIG. 1.

DESCRIPTION OF SPECIFIC EMBODIMENT

Referring to the drawings, bone fixation nail or rod 10 comprises an elongated nail body 12 having a proximal end 14 and a distal end 16. Central bore 18 extends through the nail body from proximal end 14, through a proximal portion of the nail. Bore 18 terminates at an open side groove 20 spaced between the ends of nail 10, where, in this embodiment, the bore opens to the exterior through side groove 20 at said point.

Adjacent to distal end 16, nail 10 defines a transversely flattened distal portion 22, as particularly seen in FIGS. 2 and 3, compared with FIG. 1. An open slot 24 extends centrally and longitudinally from distal end 16 along the distal portion 22 to an inner slot end 26, which is spaced between ends 14, 16 of the nail.

Nail 10 also carries a plurality of transverse holes 28, 30 extending therethrough. Transverse holes 28 are positioned adjacent to the distal end 16 of the nail, while transverse holes 30 are positioned generally perpendicular to holes 28, adjacent to proximal end 14.

One or more central transverse holes 31 may also be provided.

Central bore 18 and particularly the side aperture groove 20 that connects with central bore 18 is separated by a partition portion 32 from open communication with slot 24. Partition portion 32 is part of the rod itself, which is typically made of a known, surgically implantable metal alloy. However, if desired, central bore 20 may connect with slot 24 so that a guidewire can pass axially through the entire length of nail 10.

If desired, and as shown in FIG. 2, at least one of transverse holes 28 may carry a tapered screw 34 such as a cortical screw for locking securance of the nail 10 in the bone. Both transverse holes 28 may carry such a screw 34 in those circumstances where two of such holes are present. Thus, nail 10 may be inserted deep into the marrow or medulla of the bone, and be secured there at its distal tip with cortical locking by tapered cortical locking screws 34, or non-tapered, cylindrical screws if desired, which screws pass transversely through the bone and slot 24 of nail 10. As previously discussed, tapered screws 34 may be used to spread or distract legs 35 as they advance as desired by the surgeon.

Furthermore, if desired, a first portion 36 of the transversely flattened distal portion 22 (as in FIG. 1) may have a width that is greater than the width of a second portion 38 of the transversely flattened, distal portion 22, with first portion 36 being nearer to distal end 16 than second portion 38. The advantage of this, as described above, provides resilience to the distal end portion of the nail, permitting better fitting of the nail into the humerus, for which this particular nail is designed, or another bone.

Side edges 40 of the transversely flattened distal portion 22 are preferably smooth, and also arcuate to accommodate the varying widths 36, 38 of flattened portion 22, if present.

As is shown herein, transverse holes 30 intersect central bore 18 adjacent to proximal end 14 of nail 10. Set screws 42 each occupy a threaded portion of bore 18, being positioned to retain a cancellous bone screw 44 or the like, having threads 43 along part of their lengths. Each bone screw 44 extends through one of transverse holes 30. Each set screw 42 has an axial aperture 45 to permit a guidewire to extend completely through central bore 18 as previously described, to facilitate emplacement of nail 10 in the bone in a desired surgical manner.

Thus, nail or rod 10 can be secured to the bone which it occupies both adjacent to its proximal end 14 and its distal end 16 by the use of transverse screws.

It is further preferred for the transverse holes 30, which intersect central bore 18, to define on each side of central bore 18 (as shown in FIG. 4), a pair of axially spaced first wall sections 46 spaced along the longitudinal axis 47 of rod 10. First wall sections 46 of each hole 30 are separated by and connected with a pair of circumferentially spaced second wall sections 48. First wall sections 46 define transverse ridges which may engage threads of screw 44, or, as shown, there may be no threaded engagement, but screw 44 may merely be clamped with set screw 42 for retention. The circumferentially spaced second wall sections 48 are generally disengaged from screw 44, since the entire aperture formed by the respective wall sections 46, 48 is of a generally oval shape. Because of this, it becomes possible for screws 44 in holes 30 to rotate about a plane which is essentially perpendicular to the longitudinal axis 47 of nail 10, as shown by the dotted line position of screw 44 in FIG. 4. Because of the slightly canted portion 50 of nail 10 adjacent to proximal end 14, this plane will not be exactly horizontal from the viewpoint of FIG. 1. Despite this, screw 44 cannot be rotated up and down, parallel to axis 47. Screws 44 are shown oversized relative to holes 30, being actually removable from holes 30.

However, as previously described, this capability to (essentially) horizontally rotate screws 44 as nail 10 is being emplaced facilitates the attachment and securance of nail 10 within and to the bone, such as the humerus. Then, when screws 44 have been properly secured, set screws 46 may be rotated and advanced to provide added securance and rigidity to the entire system by pressing against screws 44 and retaining them in rigid manner relative to nail 10. Set screws 30 may be of a common type that are advanceable with an Allen wrench, having a recessed, hexagonal space 52 for receiving such a wrench. Typically, until secured by set screws 42, cancellous bone screws 44 may be rotated about 15 degrees on either side, while being firmly retained against any significant vertical rotation (i.e., parallel to nail longitudinal axis 47), until set screw 42 secures them rigidly relative to nail 10.

The above has been offered for illustrative purposes only, and is not intended to limit the scope of the invention of this application, which is as defined in the claims below.

That which is claimed:

1. A nail for axial insertion into a bone for support thereof, which comprises:
an elongated nail body having a proximal end and a distal end; a central bore extending through said nail body from the proximal end along a proximal portion of said nail and terminating at a point spaced between said ends; said nail also defining a transversely flattened distal portion extending proximally from said distal end, and an open slot extending centrally and longitudinally from said distal end along said distal portion to an inner slot end spaced between said ends, said nail body defining a plurality of transverse holes extending therethrough.

2. The nail of claim 1 in which said central bore terminates at an aperture in the side wall of said nail.

3. The nail of claim 1 in which said central bore and said open slot are separated by a partition portion preventing open communication with each other.

4. The nail of claim 1 in which at least one of said transverse holes is located adjacent to said distal end and carries a tapered screw extending through said open slot for locking securance of the nail in a bone.

5. The nail of claim 1 in which a first portion of said transversely flattened distal portion has a width that is greater than the width of a second portion of said transversely flattened distal portion, said first portion being nearer to the distal end than said second portion.

6. The nail of claim 1 in which said distal portion has opposed, smooth side edges.

7. The nail of claim 1 in which at least one of said transverse holes intersects said central bore, and a set screw occupies said bore in a position to retain a bone screw extending through said one traverse hole, said set screw having an axial aperture to permit a guidewire to extend completely through said central bore.

8. The nail of claim 1 in which at least one of said transverse holes intersects said central bore said hole defining, on each side of said central bore, axially spaced first wall sections separated by and connected with circumferentially spaced second wall sections, said first wall sections being proportioned to permit threaded engagement of a screw in said transverse hole while the screw is disengaged from said second wall sections, allowing said screw to rotate through an arc in a plane essentially perpendicular to the longitudinal axis of said nail.

9. The nail of claim 8 in which said at least one of said transverse holes has a set screw that occupies said bore in a position to retain a bone screw extending through said one traverse hole, said set screw having an axial aperture to permit a guidewire to extend completely through said central bore.

10. The nail of claim 9 in which at least one of said transverse holes is located adjacent to said distal end and carries a tapered screw extending through said open slot for locking securance of the nail in a bone.

11. A nail for axial insertion into a bone for support thereof, which comprises:
an elongated nail body having a proximal end and a distal end; a central bore extending through said nail body from the proximal end along a proximal portion of said nail and terminating at a point spaced between said ends at an aperture in the side wall of said nail; said nail also defining a transversely flattened distal portion extending proximally from said distal end, and an open slot extending centrally and longitudinally from said distal end along said distal portion to an inner slot end spaced between said proximal and distal ends, said nail body defining a plurality of transverse holes extending therethrough, a first portion of said transversely flattened distal portion having a width that is greater than the width of a second portion of said transversely flattened distal portion, said first portion being nearer to the distal end than said second portion.

12. The nail of claim 11 in which said distal portion has opposed, smooth, arcuate side edges.

13. The nail of claim 12 in which at least one of said transverse holes is located adjacent to said distal end and at least one of said transverse holes is located adjacent to said proximal end and intersecting said central bore, and a set screw occupies said central bore in a position to retain a bone screw extending through said transverse hole adjacent to said proximal end, said set screw having an axial aperture to permit a guidewire to extend completely through said central bore.

14. The nail of claim 13 in which said transverse hole adjacent to the proximal end defines, on each side of said central bore, axially spaced first wall sections, separated by and connected with circumferentially spaced second wall sections, said wall sections being proportioned to permit threaded engagement of the screw in said transverse hole by said first wall sections while the screw is disengaged from said second wall sections, allowing said screw to rotate through an arc in a plane essentially perpendicular to the longitudinal axis of said nail.

15. A nail for axial insertion into a bone for support therefor, which comprises:

an elongated nail body having a proximal end and a distal end; a central bore extending through said nail body from the proximal end at least along a proximal portion of said nail, at least one transverse hole located adjacent to said proximal end and intersecting said central bore; and a set screw that occupies said bore in a position to retain a bone screw extending through said at least one transverse hole, said set screw having an axial aperture to permit a guidewire to extend completely through said central bore.

16. The nail of claim 15 in which a distal portion of said nail is transversely flattened.

17. The nail of claim 15 in which said at least one transverse hole which intersects said central bore defines, on each side of said central bore, axially spaced first wall sections separated by and connected with circumferentially spaced second wall sections, said first wall sections being proportioned to permit threaded engagement of a screw in said transverse hole, while the screw is disengaged from said second wall sections, allowing said screw in the hole to rotate through an arc in a plane essentially perpendicular to the longitudinal axis of said nail.

18. The method of repairing a bone which comprises:

inserting a guidewire into the intramedullar space of a bone to provide a track for a nail to be subsequently advanced through the intramedullar space; advancing a nail having an elongated nail body with a central bore extending from a proximal end through at least part of said nail body, with said guidewire passing through said central bore, said guidewire also passing through an aperture in a set screw which is threadedly and rotatably retained in screw-relation within said central bore immediately proximal of a transverse hole through said nail, which hole communicates with said central bore; positioning said nail in a desired position in the bone; remaining said guidewire; transversely inserting a bone screw through said transverse hole to retain said nail and the bone together in secured relationship, and tightening said set screw against said transversely extending bone screw to firmly retain the bone screw relative to the nail.

19. The method of claim 18 in which said set screw is installed in the bore of said nail prior to placement of the nail in the bone.

20. The method of claim 18 in which other bone screws are inserted through other transverse holes of said nail to secure said nail to the bone.

21. The method of installing a nail in the intramedullar space of a bone, said nail having proximal and distal ends and an open slot extending centrally and longitudinally from said distal end proximally to an inner slot end spaced between said ends, which method comprises: inserting said nail into the intramedullar space, and securing said nail to the bone with transversely positioned bone screws that extend through said nail, including the step of passing a tapered bone screw transversely though said open slot and rotating said tapered bone screw to advance said bone screw and to distract outwardly portions of said nail which are adjacent to said open slot.

* * * * *

UNITED STATES PATENT AND TRADEMARK OFFICE
CERTIFICATE OF CORRECTION

PATENT NO. : 6,123,708
DATED : September 26, 2000
INVENTOR(S) : Thomas N. Kilpela, Clayton R. Perry, Kenneth A. Davenport, Matthew N. Songer It is certified that error appears in the above-identified patent and that said Letters Patent is hereby corrected as shown below:

Column 2,
Line 58, "Side" should be --side--.

Column 3,
After line 55, add --Thus, by this invention, a bone may be repaired by the method which comprises: inserting a guidewire into the intramedullar space of a bone to provide a track for a nail to be subsequently advanced through the intramedullar space; advancing a nail through an elongated nail body with a central bore extending from a proximal end through at least part of said nail body, with said guidewire passing through said central bore, said guidewire also passing through an aperture in a set screw which is threadedly and rotatably retained in screw-relation within said central bore immediately proximal of a transverse hole through said nail, which hole communicates with said central bore; positioning said nail in a desired position in the bone; removing said guidewire; transversely inserting a bone screw through said transverse hole to retain said nail and the bone together in secured relationship; and tightening said set screw against said transversely extending bone screw to firmly retain the bone screw relative to the nail.

The set screw may be installed in the bore of the nail prior to the placement of the nail in the bone. Also, other bone screws may be inserted through other transverse holes of the nail to secure the nail to the bone.

As another aspect of this invention, the nail of this invention may be used in a method of installation in the intramedullar space of a bone, which comprises the steps of: inserting the nail into the intramedullar space, and securing the nail to the bone with transversely positioned bone screws that extend through the nail, including the step of passing a tapered bone screw transversely through the open slot and rotating the tapered bone screw to advance the bone screw and to distract outwardly portions of the nail which are adjacent to the open slot.--

UNITED STATES PATENT AND TRADEMARK OFFICE
CERTIFICATE OF CORRECTION

PATENT NO. : 6,123,708
DATED : September 26, 2000
INVENTOR(S) : Thomas N. Kilpela, Clayton R. Perry, Kenneth A. Davenport, Matthew N. Songer It is certified that error appears in the above-identified patent and that said Letters Patent is hereby corrected as shown below:

Column 5,
Line 31, "46" should be --42--.

Column 8,
Line 9, "remaining" should be --removing--.

Signed and Sealed this

Third Day of July, 2001

*Attest:*

*Attesting Officer*

NICHOLAS P. GODICI
*Acting Director of the United States Patent and Trademark Office*